United States Patent [19]

Brockhaus et al.

[11] Patent Number: 4,469,887

[45] Date of Patent: Sep. 4, 1984

[54] PROCESS FOR THE PRODUCTION OF METHACRYLIC ACID FROM ISOBUTYRALDEHYDE

[75] Inventors: Rudolf Brockhaus, Marl; Hans-Jürgen Franke, Dorsten, both of Fed. Rep. of Germany

[73] Assignee: Chemische Werke Huels, AG, Marl, Fed. Rep. of Germany

[21] Appl. No.: 436,768

[22] Filed: Oct. 26, 1982

Related U.S. Application Data

[63] Continuation-in-part of Ser. No. 357,126, Mar. 11, 1982, Pat. No. 4,403,098.

[30] Foreign Application Priority Data

Oct. 27, 1981 [DE] Fed. Rep. of Germany ....... 3142487

[51] Int. Cl.$^3$ .................... C07C 57/065; C07C 51/27; C07C 45/58; C07D 301/06
[52] U.S. Cl. .................................. 562/599; 549/532; 562/531; 568/483; 568/594; 568/691
[58] Field of Search ................. 562/599, 531; 549/532

[56] References Cited

U.S. PATENT DOCUMENTS

| | | | |
|---|---|---|---|
| 2,389,950 | 11/1945 | Bremner et al. | 562/531 |
| 2,587,906 | 3/1952 | Schmidt | 562/531 |
| 2,942,007 | 6/1960 | Griffin et al. | 549/532 |
| 3,284,494 | 11/1966 | Schoenbrunn | 562/531 |
| 3,562,320 | 2/1971 | Woodward et al. | 562/599 |
| 3,666,805 | 5/1972 | Völker et al. | 562/599 |
| 4,403,098 | 9/1983 | Brockhaus et al. | 549/532 |

OTHER PUBLICATIONS

Migrdichian Organic Synthesis, vol. 1, p. 257, N.Y., Reinhold, 1957.
Stanford Research Institute, SRI, vol. 11, 27–37.

Primary Examiner—Natalie Trousof
Assistant Examiner—Patricia M. Scott
Attorney, Agent, or Firm—Millen & White

[57] ABSTRACT

To produce methacrylic acid, firstly, isobutyraldehyde is acetalized. The resultant acetal is cleaved into the isobutenyl ether and alcohol. The isobutenyl ether is oxidized with molecular oxygen or an oxygen-containing gaseous mixture in the presence of an alkaline solution at temperatures of 30°–70° C. to obtain the epoxide. This epoxide is hydrolyzed to the α-hydroxyisobutyraldehyde. The latter is then oxidized with concentrated or fuming nitric acid at temperatures of 20°–110° C. to produce α-hydroxyisobutyric acid, and methacrylic acid is obtained therefrom by splitting off water.

7 Claims, No Drawings

PROCESS FOR THE PRODUCTION OF METHACRYLIC ACID FROM ISOBUTYRALDEHYDE

CROSS REFERENCE TO RELATED APPLICATIONS

This application is a continuation in part application of U.S. Ser. No. 357,126, filed on Mar. 11, 1982, now U.S. Pat. No. 4,403,098.

BACKGROUND OF THE INVENTION

Methacrylic acid and its esters are valuable raw material monomers for many polymerizations. The acids or its esters are normally prepared from acetone and hydrogen cyanide according to the so-called cyanohydrin method. Acetone cyanohydrin is reacted in concentrated sulfuric acid to obtain the methacrylamide sulfate. The continued reaction to methacrylic acid or its esters is likewise a generally practiced industrial procedure (Stanford Research Institute SRI, vol. 11, pages 27 et seq.). In this synthesis, ammonium sulfate is necessarily formed together with methacrylic acid or its esters. This is an obnoxious accompanying product, usable to a limited extent as a fertilizer. In addition to the formation of this by-product, this process is disadvantageous in that it requires working with poisonous hydrogen cyanide in the first stage. These facts have given rise to numerous efforts to provide a different method of synthesis.

Attempts have been made to oxidize isobutylene by way of methacrolein to obtain methacrylic acid. The yields obtained thus far, and the technical expenses involved in this two-stage gaseous phase oxidation process (SRI Report 11: 35-37) are not as yet adequate to provide a general, large-scale industrial process based on isobutene.

It has furthermore been proposed first to prepare tertbutanol from isobutene, then to react this alcohol in the gaseous phase to methacrolein, and to convert the latter to methacrylic acid (Hydrocarbon Processing, Feb. 1979, pages 105-107). Thus far, this process has likewise been unsuitable as a substitute for the cyanohydrin process.

Finally, several other processes have become known (Stanford Research Institute Report, 11: 30) for oxidizing isobutene with nitric acid or a mixture of nitric acid and nitrogen dioxide, or mixtures thereof with acetic acid, to obtain α-hydroxyisobutyric acid, a precursor of methacrylic acid. By splitting off water, methacrylic acid is obtained from α-hydroxyisobutyric acid (German Pat. No. 1,568,948=British Pat. No. 1,080,473 and Canadian Pat. No. 771,714; DOS No. 1,768,253=British Pat. No. 1,179,987).

Although these methods produce, in part, quite satisfactory yields based on butene, the reaction solutions and intermediate products are explosive. Furthermore, the nitrogen-oxygen compound involved is reduced to $N_2$ or $N_2O$, rather than to NO. However, only NO, in contrast to $N_2$ or $N_2O$, can be reoxidized with atmospheric oxygen and recycled as nitric acid, thus providing desirable economy.

In the past, efforts have also been expended to dehydrogenate isobutyric acid to methacrylic acid (German Pat. No. 2,129,920=British Pat. No. 1,332,558; German Pat. No. 2,208,580=British Pat. No. 1,360,550). This procedure likewise has failed to produce technically satisfactory results.

Therefore, great interest still exists in finding an improved process for preparing methacrylic acid from readily accessible starting materials in a technically simple way and in good yields.

SUMMARY OF THE INVENTION

Accordingly, it is an object of this invention to provide such an improved process.

Upon further study of the specification and appended claims, further objects and advantages of this invention will become apparent to those skilled in the art.

These objects have been attained by this invention by providing a process for preparing methacrylic acid from isobutyraldehyde in several stages, comprising, 1. in a first stage, acetalizing isobutyraldehyde in a conventional fashion,
2. in a second stage, conventionally cleaving the acetal into isobutenyl ether and alcohol,
3. oxidizing the isobutenyl ether to the epoxide with molecular oxygen or an oxygen-containing gaseous mixture in the presence of 50-500 ppm of an alkaline solution, at temperatures of 30°-70° C.,
4. conventionally hydrolyzing the epoxide to a α-hydroxyisobutyraldehyde,
5. subsequently oxidizing this product to a-hydroxyisobutyric acid with 1.2-2 moles of fuming of concentrated nitric acid per mole of aldehyde at temperatures of 20°-110° C., and
6. obtaining methacrylic acid conventionally from the α-hydroxyisobutyric acid by splitting off water.

DETAILED DISCUSSION

Stages 3 and 5 of the process of this invention are per se novel.

The process of this invention can be schematically illustrated below:

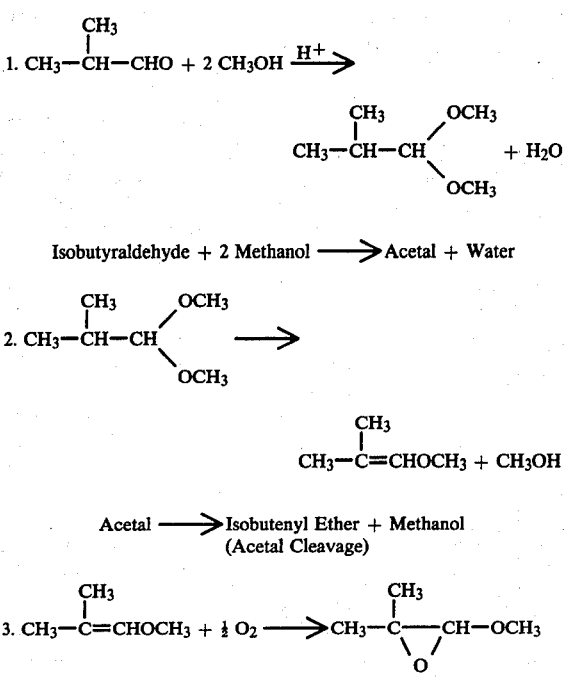

Oxidation of isobutenyl ether with molecular oxygen to the epoxide (isobutenyl oxide methyl ether).

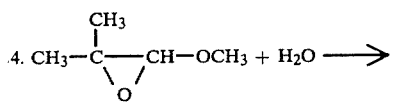

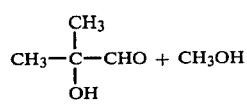

Addition of water to the epoxide with the formation of α-hydroxyisobutyraldehyde and methanol.

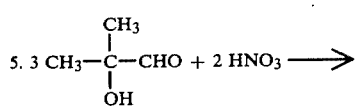

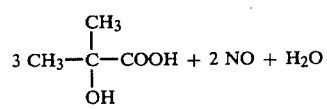

Oxidation of a α-hydroxyisobutyraldehyde with nitric acid to α-hydroxyisobutyric acid.

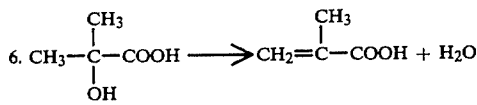

Splitting off water from α-hydroxyisobutyric acid to obtain methacrylic acid.

The acetal formation (stage 1) is effected by reaction of isobutyraldehyde with an alcohol (e.g., a not branched $C_1$-$C_4$-alkanol), preferably methanol, generally in approximately stoichiometric amounts. The acetal formation takes place conventionally in the presence of acidic catalysts, e.g., 0.01–1,5% by weight of p-toluenesulfonic acid or sulfuric acid, based on the amount of starting material, or alternatively on ion exchangers and at temperatures of 60°–100° C.

In general, the isobutyraldehyde is combined with the alcohol at temperatures of 10°–30° C., and the mixture is thereafter heated to 60°–100° C. The equilibrium is at a conversion of 60–70% and is obtained within a few minutes. Subsequently, the acidic catalyst is neutralized with the stoichiometric quantity of an alkaline solution, for example NaOH, or alternatively the ion exchanger is removed. To separate off the unreacted alcohol and isobutyraldehyde, the reaction product is, for example, washed repeatedly with water. The washed product is distilled. The washing water can be stripped to recover isobutyraldehyde and alcohol, e.g., methanol. This stage is fully conventional unless indicated otherwise herein: see, e.g., Kirk Othmer, Encyclopedice of Chemical Technology (1947), Vol. 1, page 43–45 whose disclosure is incorporated by reference herein.

The cleavage of the resultant dewatered acetal to the isobutenyl ether (stage 2) takes place directly or in an inert diluent, such as paraffin oil and the like, in the presence of 0,01–1% by weight of acidic catalyst based on the amount of ether, e.g., p-toluenesulfonic acid, at temperatures of 80°–150° C. and for times, e.g., of 3–60 min. The mixture of ether and alcohol, preferably methanol, is continously removed by distillation during the cleavage reaction. The ether is freed of the alcohol by washing with water, optionally dried, and distilled. The alcohol can be removed from the water by striping. The second stage per se is also fully conventional unless indicated otherwise herein; see, e.g., L. Claisen, Ber. dtsch. Chem. Ges. 31, 1021 (1898); DRP No. 525 836 (1929) whose disclosure is incorporated by reference herein.

The yields of the first two steps depend on the intensity of alcohol, especially methanol, and isobutyraldehyde recovery from the water, and are 90–95 mole %. Without water processing, a yield of about 40% is obtained. The separation of water between stage 1 and 2 is necessary, because the acetal hydrolysies volontary in the presence of water and $H^+$ ions to aldehyde, the enol ether is mainly formed in absence of water.

Stage 3, the oxidation of the unsaturated ether with molecular oxygen or an oxygen-containing gaseous mixture, such as air, in the presence of an alkaline solution at temperatures of 30°–70° C. is novel and unexpected.

Heretofore, use of the substantially more expensive peroxides has been required for such an epoxidation. Accordingly, this stage provides a surprising advance in the art. As is generally the case in oxidations, the selectivity is a function of the conversion and drops with rising conversion. Minor amounts of acetone and alkyl formate as well as α-hydroxyisobutyraldehyde acetal are formed as by-products.

Acetone is a useful by-product, and is obtained in a quantity of 10–20%, based on the epoxide. Another by-product is α-hydroxyisobutyraldehyde acetal which can be processed as well in the further process stages. This is a significant advantage. There is practically no production of CO and $CO_2$ during oxidation. The alkaline solution which is added is inexpensive. Moreover, this reaction solution simultaneously stabilizes the thus-formed epoxide.

The oxidation of the isobutenyl ether (stage 3) to the isobutenyl oxide ether is preferably conducted in an oxidizing reactor for liquid-phase oxidation, for example, in a bubble column reactor. The isobutenyl ether is gas-treated with molecular oxygen in the presence of 50–500 ppm of an alkaline solution in the startin ether, at temperatures of 30°–70° C., preferably 40°–50° C., generally for times of 2–20 min. Larger quantities of alkaline solution do not provide any improvement. Herein, the term "alkaline solution" includes the solution which results when the mentioned quantity of alkaline reagent per se ist directly added to the starting material ether. In all cases, 50–500 ppm of alkaline reagent per se is intended.

Suitable alkaline solutions include system compatible hydroxides such as those of the alkali and alkaline earth metals, in alcoholic or also aqueous solutions, preferably KOH and NaOH. Typically, alkaline solution strengths are 10–50 wt%, based on the total amount of water or alcohol and alkaline reagent. The molecular oxygen employed can be substantially pure molecular oxygen or an oxygen-containing gaseous mixture, preferably air. The oxygen is preferably introduced into the reaction in finely dispersed form, for example, by way of a porous plate.

The waste gas from the oxidation contains unreacted oxygen and/or unreacted oxygen-containing gaseous mixture, but has practically no CO or $CO_2$. Readily boiling compounds discharged with the waste gas, such as, for example, methanol, acetone, and alkyl formate can be separated in a cooling system.

It is advantageous to begin the oxidation at a temperature of 30°–50° C. with a relatively large amount of 15–20 liters of molecular oxygen per kilogram of isobutenyl ether, and complete the oxidation, with continuous adaptation to the conversion-dependent reaction velocity, after a conversion of 80–90% at a temperature of 55°–70° C., preferably up to 60° C., and with an oxygen quantity of 5–10 l/kg of isobutenyl ether. With this procedure, an almost complete oxygen conversion is obtained. (For a further description of such a procedure per se, see, e.g., Ullmanns Encyklopädie der techn. Chemie, 4. Aufl. Vol. 1, pages 193–195). Any further temperature increase reduces the selectivity of the reaction and results in loss of product. Such loss of product can be reduced by operating under pressure, but this requires undesirable technical expense.

The crude epoxide can be directly processed further, but it can also be first purified by distillation. For the neutralization of any organic acids formed and for epoxide stabilization, the discharge from the reactor is combined with 0.5–2.5% by weight of an alkaline solution, preferably KOH or NaOH in a small amount of methanol (solution strength of about 10–50 wt%), and a fractionation is carried out under reduced pressure. Firstly, the unreacted ether is distilled off, preferably under a pressure of 250–300 bar. The epoxide is preferably distilled under a pressure of 1–30 mbar. The purity is 95–99% epoxide.

For the hydrolysis (stage 4), the pure epoxide or the crude epoxide can be utilized together with any α-hydroxyisobutyraldehyde acetal, which follows as the next run in the distillation. For purposes of hydrolysis, water is provided in a quantity of 1:1–1.8 moles per mole of epoxide, and the epoxide is gradually added under agitation at a temperature of 60°–66° C. The reaction temperature is maintained by cooling and/or by boiling the alcohol obtained during the reaction, which generally ensues for 3–60 minutes.

After the reaction, it is suitable, but not a necessity of the process, to recover the primary amount of alcohol, for example methanol, by striping, perhaps for the purpose of ensuring hydrolysis of by-product acetal in a weakly acidic medium derived from addition of HNO$_3$ during the striping. The residual alcohol forms esters in the subsequent oxidation stage, especially with nitrous acid. The optimum amount of water depends on the degree of hydrolysis desired (e.g., 99–100%), on the one hand, and on the amount of dilution, impairing the subsequent HNO$_3$ oxidation, usually a minimum of 3–15% residual water, based on α-hydroxyisobutyraldehyde, being used. This stage is fully conventional unless indicated otherwise herein; see, e.g., Ullmanns Encyklopädie der techn. Chemie, 4. Aufl., Vol. 8, page 201–202 whose disclosure is incorporated by reference herein.

In the novel nitric acid oxidation stage 5, the gases escaping after oxidation, surprisingly, contain essentially only the nitrogen oxides NO and NO$_2$, in contrast to the prior art processes (SRI Report op.cit.) as well as esters, especially nitrous acid esters, if residues of methanol are present. Only small amounts of N$_2$ and N$_2$O are formed. This is a considerable advantage over these previous methods, because nitric acid thus serves as a regenerable oxygen transfer agent. The nitric acid employed can be commercially available, concentrated (e.g., 65%) or fuming acid.

The subsequent oxidation of the α-hydroxyisobutyraldehyde (stage 5) takes place directly after the hydrolysis or with the residue remaining therefrom after removing the alcohol by distillation. The oxidation is carried out with fuming or concentrated nitric acid at temperatures of 20°–110° C. with a quantity of 1.2–2 moles of nitric acid per mole of aldehyde, preferably without addition of catalyst, e.g., for 3–90 minutes. The addition of customary nitric acid oxidation catalysts, such as cerium salts or vanadium compounds, is possible, but not necessary. (In this regard, see, Fieser, Lehrbruch der Organischen Chemie, Verlag Chemie (1954) pages 211–212) whose disclosure is herein incorporated by reference.)

By-products contained in the crude epoxide, such as, for example, α-hydroxyisobutyraldehyde dimethylacetal are oxidized to the desired final product. Either the nitric acid or the α-hydroxyisobutyraldehyde can be first charged into the reactor. A lower concentration can be compensated for by a higher reaction temperature. In stages 4 and 5, yields are obtained in total of ≧95 mol%, based on the details of these epoxide hydrolysis and oxidation stages per se.

The crude product from this oxidation stage is preferably fractionated at 1–200 mbar vacuum pressure. After a forerun consisting essentially of water and nitric acid, the α-hydroxyisobutyric acid is obtained in a pure white and crystalline form. This acid has a melting point of ≧75° C. There is practically no yield of acetic acid. Methacrylic acid is not as yet produced in this stage.

The step of splitting off water from α-hydroxyisobutyric acid to obtain methacrylic acid (stage 6) takes place conventionally, for example according to the disclosure of German Pat. No. 1,568,948=British Pat. No. 1,080,473; Canadian Pat. No. 771,714; and DOS No. 1,768,253=British Pat. No. 1,179,987, all of whose diclosures are incorporated by reference herein.

For example, α-hydroxyisobutyric acid can be heated in the presence of its metallic salts, preferably the salts of the alkali and alkaline earth metals, under atmospheric pressure to about 200° C. in a distillation flask with a column attached thereto. Under these conditions, the α-hydroxyisobutyric acid is dehydrated. The reaction products, which are distilled over at 93°–157° C., contain methacrylic acid in a yield of about 95%. The methacrylic acid is separated from the water in the distillate by means of fractional distillation.

The process of this invention has the special advantage that only readily accessible starting materials are required. The raw material isobutyraldehyde can be obtained in the oxo synthesis, in part in considerable quantities, being formed from propylene and synthesis gas. The only other raw material required is oxygen and/or air, in part by way of HNO$_3$ as the O$_2$ transfer agent. The alcohol, especially methanol, is recirculated. One kilogram of isobutyraldehyde yields, by way of all stages, ≧0.75 kg of methacrylic acid.

The methacrylic acid is required commercially, in part, directly, and to a larger degree as the ester. Esterification after the last stage, or in combination with this last stage, is likewise possible, fully conventionally.

All stages can be conducted continuously or discontinuously. The process of this invention is very beneficial from an ecological viewpoint. Working with the dangerous hydrogen cyanide is avoided. Furthermore, no appreciable amounts of by-products are formed, besides acetone and alkyl formate. The methacrylic acid is obtained in great purity, so that this acid or its esters can be utilized directly for polymerization to obtain polymethacrylates.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

1.1 Acetal Formation
1.1.1 Acetalization with p-Toluenesulfonic Acid

Isobutyraldehyde and methanol are combined in stoichiometric amounts at 25° C. in the presence of 0.3% by weight of p-toluenesulfonic acid, based on the amount of starting mixture. While heating to about 60° C., equilibrium is obtained within a few minutes (60–70% conversion). The acid is neutralized with the stoichiometric quantity of NaOH. The reaction product is washed repeatedly with water to separate unreacted methanol and isobutyraldehyde. The washed product is distilled. The acetal passes over at 100°–104° C. The organic components contained in the washing water are recovered by distillation.

1.1.2 Acetalization with Ion Exchanger 450 g/h of an isobutyraldehyde/methanol mixture (50 mol% isobutyraldehyde and 50 mol% methanol) is continuously introduced into a pipe coil reactor filled with 250 ml of an acidic ion exchanger (based on crosslinked, sulfonated styrene polymers); pipe inner diameter; 10 mm; pipe length: 4 m. The reaction temperature is maintained at 100° C., the operating pressure at 5 bar. The continuously obtained reaction product contains, besides unreacted isobutyraldehyde and methanol, the desired acetal, isobutenyl methyl ether, and reaction water. The reaction product is worked up as described in Example 1.1.1.

1.2 Acetal Cleavage to the Isobutenyl Methyl Ester
1.2.1 Cleavage

Isobutyraldehyde dimethylacetal is brought to boiling with 0.5% p-toluenesulfonic acid in a distillation flask with column attached thereto (sump temperature 100° C.). Due to the onsetting cleavage of the acetal to the isobutenyl methyl ether and methanol, a temperature of 55°–57° C. is reached in the vapor phase. At this temperature, the low-boiling cleaved product mixture is distilled off. The ether is freed of methanol by a water washing step, dried, and distilled. The ether boils at 75°–77° C. The methanol is obtained from the water by further distillation.

The yield of the first two stages depends on the intensity of the methanol-isobutyraldehyde recovery from the water and ranges between 90 and 95 mol%. A yield of 40% is obtained without the step of working up with water.

1.2.2 Cleavage with Addition of Paraffin Oil

Isobutyraldehyde dimethylacetal is heated with 0.5% p-toluenesulfonic acid and with paraffin oil in an alembic with column attached thereto (weight ratio acetal: paraffin oil=1:0.4, sump temperature 100°–120° C.). The batch is heated, and the mixture of ether and methanol is distilled off continuously.

The ether is obtained in the pure form and the methanol is recovered as described in Example 1.2.1.

1.3 Oxidation of the Isobutenyl Methyl Ether with Formation of Isobutenyl Oxide Methyl Ether

1.3.1 Ether Oxidation with Pure Oxygen

In an oxidizing apparatus, the reaction portion of which consists of a forced circulation reactor with a reaction tube having an internal diameter of 40 mm, a height of 2000 mm, and a temperature-controllable product circulation, 2,660 g of isobutenyl methyl ether containing 200 ppm of KOH is gas-treated at 34° C. with 50 l/h of pure, molecular oxygen. The oxygen passes into the reaction tube at the bottom by way of a porous plate. The waste gas contains unreacted oxygen, but practially no CO or $CO_2$. Low-boiling compounds discharged from the reactor, such as, for example, acetone and methyl formate, are condensed in a cooling system. With an ether conversion of about 40%, the reaction temperature is increased along a sliding scale to 55° C. in order to obtain an almost complete oxygen conversion, and the oxygen feed is continuously reduced from 50 l/h to 10 l/h.

The following values were obtained for conversion and yield:

| % Conversion/ Ether | Yield (mol %) | | | |
|---|---|---|---|---|
| | Epoxide | Methyl formate | Acetone | α-Hydroxy-isobutyraldehyde Dimethyl Acetal |
| 67 | 75 | 1 | 10 | 3 |
| 88 | 69 | 1.5 | 18 | 5 |

The discharge from the reactor is then combined with 0.3% by weight of KOH—dissolved in a small amount of methanol—and the mixture is fractionated at vacuum pressure. At 300 mbar the unreacted ether, acetone, and methyl formate are removed by distillation; the epoxide boils at 150 mbar and 45°–46° C. The purity is 95% epoxide.

1.3.2 Ether Oxidation with Air 2,750 g of isobutenyl methyl ether is charged with 500 ppm of potassium hydroxide into the above-described oxidation reactor. At a reaction temperature of 50° C., the charge is gas-treated with 80 l/h of air. The air passes into the reaction tube from the bottom by way of a porous plate. Low-boiling compounds discharged from the reactor with the waste gas, such as, for example, unreacted ether, acetone, and methyl formate, are condensed in a cooling system and recycled into the reactor. With an ether conversion of about 40%, the reaction temperature is increased along a sliding scale to 60° C. in order to maintain the almost complete oxygen conversion, and the air feed is reduced, likewise on a sliding scale, to 20 l/h. The reaction product is worked up as described in Example 1.3.1. The yields correspond to those of the oxygen oxidation.

1.4 Water Addition to the Epoxide with Formation of α-Hydroxyisobutyraldehyde

1.4.1 Hydrolysis of Distilled Epoxide.

The epoxide fraction, after evaporation of the ether and the produced low-boiling compounds, is hydrolyzed together with α-hydroxyisobutyraldehyde dimethylacetal, following as the next run during the distillation. For this purpose, the stoichiometric amount of water with a 10% excess is charged into the flask, and gradually blended under agitation within a time of about 60 minutes with the epoxide. The reaction temperature is maintained at 66° C. by cooling. After the evolution of heat has ceased, the content of the flask is gently superficially distilled and adjusted with $HNO_3$ to pH 3. During this step, the methanol is removed. The remaining residue is directly employed in the nitric acid oxidation step.

1.4.2 Hydrolysis of Crude Epoxide 320 g of water is charged into a flask and mixed under agitation with 1,700 g of crude epoxide, such as, for example, the oxidation product in Example 1.3.2 (duration: 30 minutes). The reaction temperature is maintained at 66° C. by slight cooling and ensuing methanol and low-boiler reflux. After the heat evolution has ceased, the reaction product is superficially distilled to remove unreacted ether, methanol, and low-boiling compounds present from the starting material.

1.5 Nitric Acid Oxidation 1.5.1 Oxidation with 100% Nitric Acid 500 g of residue from the hydrolysis with 3.6 moles of aldehyde and 0.9 mole of a α-hydroxyisobutyraldehyde dimethylacetal is heated in a flask to 70° C. and combined with 5.8 moles of 100% nitric acid (fuming acid). The temperature is kept at 80° C. by cooling. The escaping gases are essentially NO, $NO_2$, and, depending on the methanol content, esters, primarily nitrous acid esters. $N_2$ and $N_2O$ only appear in traces. After the evolution of heat and gas has ceased, the liquid product is distilled under vacuum. A forerun is removed at 200–15 mbar which consists mainly of water and $HNO_3$. At 0.5–1 mbar, the white α-hydroxyisobutyric acid, in the process of crystallizing, boils at a heat temperature of about 90° C. In a simple laboratory bridge, about 80% of the α-hydroxyisobutyric acid passes over as 95% strength acid, melting point 75° C.

The yield of α-hydroxyisobutyric acid by way of the steps of epoxide hydrolysis—nitric acid oxidation is 90–95 mol%.

1.5.2 Oxidation with 65% Nitric Acid 980 g of concentrated 65% nitric acid is charged into a flask under agitation at 20° C. Then within 45 minutes, 500 g of crude α-hydroxyisobutyraldehyde—4.4 moles of aldehyde, 0.7 moles of α-hydroxyisobutyraldehyde dimethylacetal with 3.3 moles of water—is continuously added thereto. Evolution of heat and gas commences immediately. The temperature is maintained at about 40° C. by cooling. After the addition of aldehyde is completed, the batch is maintained at 60°–70° C. for about 30 minutes to complete the reaction, and then worked up as described in Example 1.5.1. The yield of α-hydroxyisobutyric acid is 4.85 moles.

1.6 Splitting off Water from α-Hydroxyisobutyric Acid to Obtain Methacrylic Acid 350 g of α-hydroxyisobutyric acid (96.5%), 6 g of sodium hydroxide, and 0.6 g of hydroquinone methyl ether are introduced into a distillation flask with a column attached thereto, and heated to boiling to about 200° C. During this step, air is fed into the distillation flask at a rate of 50 ml/minute. The reaction products passing over by distillation at 92°–130° C. contain methacrylic acid in a yield of 95%. The methacrylic acid is separated from the concomitantly obtained water by fractional distillation. The sodium hydroxide reacts with α-hydroxyisobutyric acid to form the sodium salt of this acid, which salts acts as a dehydration catalyst.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A multi-stage process for producing methacrylic acid from isobutyraldehyde, comprising:
   (a) acetalizing isobutyraldehyde with a not branched $C_{1-4}$-alkanol in the presence of an acidic catalyst, to form the corresponding isobutyraldehyde acetal;
   (b) cleaving the latter acetal in the presence of an acidic catalyst to form the corresponding isobutenyl ether and alcohol;
   (c) oxidizing the isobutenyl ether to form the corresponding epoxide by reacting it with $O_2$ in the presence of 50–500 ppm of an alkali or alkaline earth metal hydroxide at a temperature of 30°–70° C.;
   (d) hydrolyzing the epoxide to form a α-hydroxyisobutyraldehyde;
   (e) oxidizing the latter product with 1.2–2 moles of nitric acid per mole of aldehyde at a temperature of 20°–110° C. to form α-hydroxyisobutyric acid; and
   (f) splitting-off water from the latter to produce methacrylic acid.

2. A process of claim 1, wherein, in step (c), KOH or NaOH is used as the hydroxide.

3. A process of claim 1, wherein, in step (c), $O_2$ is employed in the form of substantially pure molecular oxygen.

4. A process of claim 1, wherein, in step (c), $O_2$ is employed in the form of an $O_2$-containing gas mixture.

5. A process of claim 4, wherein the gas mixture is air.

6. A process of claim 1, 2, 3 or 5 wherein, in step (c), the oxidation of the isobutenyl ether is begun at a temperature of 30°–50° C. using an amount of oxygen of 15–20 l/kg of isobutenyl ether, and is completed after a conversion of 80–90% by a continuous adaptation of the conversion-dependent reaction velocity by increasing the temperature to 55°–70° C. and substantially proportionally decreasing the amount of oxygen to 5–10 l/kg of isobutenyl ether.

7. A process of claim 6, wherein, in step (a), the alkanol is methanol, the acidic catalyst is p-toluenesulfonic acid or sulfuric acid in an amount of 0.01–1,5 wt% and the reaction is carried out at a temperature of 60°–100° C.;

wherein, in step (b), the acidic catalyst is p-toluenesulfonic acid and the reaction temperature is 80°–150° C.;

wherein, in step (c), the temperature increase is begun at an ether conversion of about 40 mol%;

wherein, in step (d), the hydrolysis is conducted with 1.1–1.8 moles of water per mole of epoxide and at a temperature of 60°–66° C.;

wherein, in step (e), the nitric acid is used in the form of fuming or concentrated nitric acid; and wherein, in step (f), the split-off of water is conducted by converting α-hydroxyisobutyric acid to an alkali or alkaline earth metal salt thereof and heating the latter to about 200° C.

* * * * *